US009125596B2

(12) United States Patent
Leclerc et al.

(10) Patent No.: US 9,125,596 B2
(45) Date of Patent: Sep. 8, 2015

(54) NANOSTRUCTURE-INITIATOR MASS SPECTROMETRY BIOMETRICS

(71) Applicant: The Regents of the University of California, Oakland, CA (US)

(72) Inventors: Marion Leclerc, Berkeley, CA (US); Benjamin Bowen, Walnut Creek, CA (US); Trent Northen, Walnut Creek, CA (US)

(73) Assignee: The Regents of the University of California, Oakland, CA (US)

( * ) Notice: Subject to any disclaimer, the term of this patent is extended or adjusted under 35 U.S.C. 154(b) by 540 days.

(21) Appl. No.: 13/631,687

(22) Filed: Sep. 28, 2012

(65) Prior Publication Data

US 2014/0247115 A1 Sep. 4, 2014

Related U.S. Application Data

(60) Provisional application No. 61/540,794, filed on Sep. 29, 2011.

(51) Int. Cl.
| | |
|---|---|
| *A61B 5/117* | (2006.01) |
| *G06K 9/00* | (2006.01) |
| *H01J 49/04* | (2006.01) |
| *A61B 5/00* | (2006.01) |
| *H01J 49/00* | (2006.01) |
| *A61B 5/145* | (2006.01) |

(52) U.S. Cl.
CPC ........... *A61B 5/1172* (2013.01); *A61B 5/14507* (2013.01); *A61B 5/14546* (2013.01); *A61B 5/4845* (2013.01); *A61B 5/4848* (2013.01); *A61B 5/6826* (2013.01); *G06K 9/0053* (2013.01); *G06K 9/00885* (2013.01); *H01J 49/0027* (2013.01); *H01J 49/0031* (2013.01); *H01J 49/04* (2013.01); *H01J 49/0418* (2013.01); *H01J 49/0463* (2013.01); *A61B 2576/02* (2013.01); *G06K 2009/00946* (2013.01)

(58) Field of Classification Search
CPC ............. A61B 5/1172; A61B 5/14546; A61B 5/4845; A61B 5/6826; A61B 5/14507; A61B 5/4848; A61B 2576/02; G06K 9/0053; G06K 9/00885; G06K 2009/00946; H01J 49/0027; H01J 49/0031; H01J 49/04; H01J 49/0418; H01J 49/0463
See application file for complete search history.

(56) References Cited

U.S. PATENT DOCUMENTS

| | | | | |
|---|---|---|---|---|
| 8,766,177 | B2 * | 7/2014 | Verbeck, IV | 250/288 |
| 2008/0128608 | A1 * | 6/2008 | Northen et al. | 250/282 |
| 2011/0151569 | A1 * | 6/2011 | Rowell et al. | 436/86 |

(Continued)

OTHER PUBLICATIONS

Rowell et al.,"Detection of drugs and their metabolites in dusted latent fingermarks by mass spectrometry", Analyst, 2009, 134, 701-707.*

(Continued)

*Primary Examiner* — Jack Berman
(74) *Attorney, Agent, or Firm* — Knobbe Martens Olson & Bear LLP

(57) ABSTRACT

Several embodiments described herein are drawn to methods of identifying an analyte on a subject's skin, methods of generating a fingerprint, methods of determining a physiological change in a subject, methods of diagnosing health status of a subject, and assay systems for detecting an analyte and generating a fingerprint, by nanostructure-initiator mass spectrometry (NIMS).

29 Claims, 12 Drawing Sheets

(56) References Cited

U.S. PATENT DOCUMENTS

2013/0341901 A1* 12/2013 Staymates et al. ............ 283/78
2014/0020447 A1* 1/2014 Badorrek et al. ............ 73/23.37
2014/0084151 A1* 3/2014 Ferguson et al. ............ 250/282

OTHER PUBLICATIONS

Ferguson et al., "Direct detection of peptides and small proteins in fingermarks and determination of sex by MALDI mass spectrometry profiling", Analyst, 2012, 137, 4686-4692.*

Northen et al. (2007) Clathrate nanostructures for mass spectrometry. Nature, 449:1033-1036.

Northen et al. (2008) A nanostructure-initiator mass spectrometry-based enzyme activity assay. Proc. Natl. Acad. Sci., 105(10):3678-3683.

Woo et al. (2008) Nanostructure-initiator mass spectrometry: a protocol for preparing and applying NIMS surfaces for high-sensitivity mass analysis. Nature Protocols, 3(8):1341-1349.

* cited by examiner

Left finger | Right finger

Right finger before touching mud

Right finger after touching mud

Right finger before exercising

Right finger after exercising

NANOSTRUCTURE-INITIATOR MASS SPECTROMETRY BIOMETRICS

CROSS-REFERENCE TO RELATED APPLICATIONS

This application claims priority under 35 U.S.C. §119(e) to U.S. Provisional Patent Application No. 61/540,794 filed Sep. 29, 2011. The contents of this related application is hereby expressly incorporated by reference in its entirety.

STATEMENT OF GOVERNMENT RIGHTS

This invention was made with government support under Contract No. DE-AC02-05CH11231 awarded by the U.S. Department of Energy. The government has certain rights in the invention.

FIELD OF THE INVENTION

Embodiments provided herein relate generally to the fields of biometrics, fingerprinting, and mass spectrometry. More particularly, several embodiments described herein are drawn to methods of identifying an analyte on a subject's skin, methods of generating a fingerprint, methods of determining a physiological change in a subject, methods of diagnosing health status of a subject, and assay systems for detecting an analyte and generating a fingerprint, by nanostructure-initiator mass spectrometry (NIMS).

BACKGROUND

Current biometrics and fingerprinting techniques can provide an image of a person's finger, capturing the traces of an impression from a finger's friction ridges caused by raised portions of the skin on the tip of the finger. Impressions of fingerprints can be left on a surface by sweat or secretion from glands present in friction ridges of a finger or can be made by transferring ink from the peaks of friction ridges to a surface, such as a fingerprint card. Fingerprints are typically used for identification purposes, particularly in forensics.

Current biometrics technology involves methods for recognizing individuals based on physical traits, such as fingerprints, face recognition, iris recognition, or retina recognition. Biometrics is typically used for verification so that an individual can be positively identified by making a one-to-one comparison of a captured biometric with a stored template. Biometrics can also be used to make a one-to-many comparison of a captured biometric against a biometric database in attempt to identify an unknown individual.

SUMMARY OF THE INVENTION

Several embodiments provided herein relate to nanostructure-initiator mass spectrometry (NIMS) biometrics assays and methods capable of providing both (1) a fingerprint image and (2) chemical information on the finger.

Several embodiments are directed to a method of identifying a subject including generating a mass spectrum from a nanostructure-initiator mass spectrometry (NIMS) chip, wherein the chip comprises an analyte from the subject's skin; identifying a mass spectrum pattern unique to the subject; and comparing the mass spectrum pattern to a known pattern, thereby identifying the subject. In one aspect, generating the mass spectrum comprises contacting the subject's skin to the NIMS chip by applying an analyte on the subject's skin to the NIMS chip, the mass spectrum comprises ions derived from the analyte, and identifying the mass spectrum pattern unique to the subject comprises detecting a pattern of the ions derived from the analyte.

Several embodiments are drawn to a method of identifying an analyte on a subject's skin including contacting the subject's skin to a nanostructure-initiator mass spectrometry (NIMS) chip; generating a mass spectrum from the chip; and identifying the analyte from the mass spectrum. In one aspect, contacting the subject's skin to the NIMS chip includes applying an analyte on the subject's skin to the NIMS chip, the mass spectrum comprises an ion derived from the analyte, and identifying the analyte from the mass spectrum includes detecting the ion. In the same aspect, the ion is unique to the analyte. In a further aspect, the analyte includes isotopes and the method further comprises identifying the origin of the analyte by determining a ratio of the isotopes indicative of the origin.

In one aspect, the analyte is a chemical, microbe, metabolite produced by the subject, endogenous biomarker, animal substance, ingested substance, or environmental substance. In some aspects wherein the analyte is a microbe, the method further includes determining the origin of the subject's exposure to the microbe based on the identification of the microbe. Furthermore, in some aspects wherein the analyte is a microbe, the method further includes identifying a community of microbes on the skin. Additionally, in some aspects wherein the analyte is a microbe, the method further includes determining the identity of the subject based on the identification of the community of microbes.

In various aspects of the aforementioned embodiments, the chemical is gunpowder, an explosive, a weapon, or a drug.

In further aspects of the aforementioned embodiments, the method further includes determining where the subject has been based on the identification of the analyte, wherein the identified analyte is indicative of a geographical location.

In additional aspects of the aforementioned embodiments, the method further includes determining what the subject has been exposed to based on the identification of the analyte. In several aspects, the skin is from the subject's finger.

In various aspects of the aforementioned embodiments, the method further includes generating an image of a print of the subject's skin on the NIMS chip. In one aspect, the method further includes generating a fingerprint image of the subject's finger.

In further aspects of the aforementioned embodiment, identifying the analyte includes detecting the ion specific to the analyte by matching the detected ion with a known ion standard.

In additional aspects of the aforementioned embodiments, the method further includes identifying a plurality of analytes on the subject's skin by detecting ions specific to the analytes, and determining a biometric pattern from the identified analytes.

Several embodiments provided herein relate to a method of generating a fingerprint including contacting the subject's finger to a nanostructure-initiator mass spectrometry (NIMS) chip, thereby applying metabolites to the NIMS chip; generating a mass spectrum at sites on the NIMS chip contacted with the finger, wherein the mass spectrum comprises ions from the metabolites applied to the NIMS chip; and reconstructing an image of the subject's finger from the mass spectrum generated at sites on the NIMS chip contacted with the finger, thereby generating a fingerprint. In one aspect, a mass spectrum is generated at every position of the NIMS chip in two dimensions at an x-y step-size of about 75 μm. In the same aspect, reconstructing an image of the subject's finger includes computationally reading each generated mass spectrum and storing the intensity information of each mass spectrum in a 2D array, wherein the first dimension represents the pixels and the second dimension represents the mass-to-charge (m/z) values of each mass spectrum.

Various embodiments provided herein are drawn to a method of determining a physiological change in a subject including generating a fingerprint of the subject at a first and one or more later times; and determining the difference in the fingerprints, which reflects a difference in mass spectrum ions at the first and later time, wherein the difference in the fingerprints indicates a physiological change in the subject. In one aspect, the physiological change is a change in health status of the subject. In the same aspect, the change in health status reflects before and after exercise. In other aspects, the change in health status reflects a change in hygiene. In the same aspect, the change in hygiene reflects hand washing. Further in the same aspect, the change in hygiene reflects use of a cleaning product. In another aspect, the change in health status reflects before and after taking medication or a healthcare product, such as an antibiotic or antibacterial agent.

In several aspects, embodiments drawn to a method of determining a physiological change in a subject further includes profiling a physiological change in the subject based on the change in fingerprints.

Several embodiments provided herein relate to a method of diagnosing health status of a subject including generating a NIMS fingerprint of the subject and determining the subject's health status by comparing the subject's fingerprint to a predetermined fingerprint profile indicative of a known health status, wherein a match between the subject's fingerprint and the predetermined fingerprint profile indicates the subject has the known health status. In various aspects, the health status reflects exercise, hygiene, taking medication or a healthcare product (e.g. an antibiotic or antibacterial agent), exposure to chemicals, or exposure to microbes.

Various embodiments provided herein are drawn to an assay system for detecting an analyte and generating a fingerprint image including a nanostructure-initiator mass spectrometry (NIMS) chip and a computational script capable of reconstructing a fingerprint from mass spectra generated at sites on the NIMS chip contacted with a finger. In one aspect, the computational script is programmed to read each generated mass spectrum from the NIMS chip and store the intensity information of each mass spectrum in a 2D array, wherein the first dimension represents the pixels and the second dimension represents the mass-to-charge (m/z) values of each mass spectrum.

DETAILED DESCRIPTION

Figure 1:
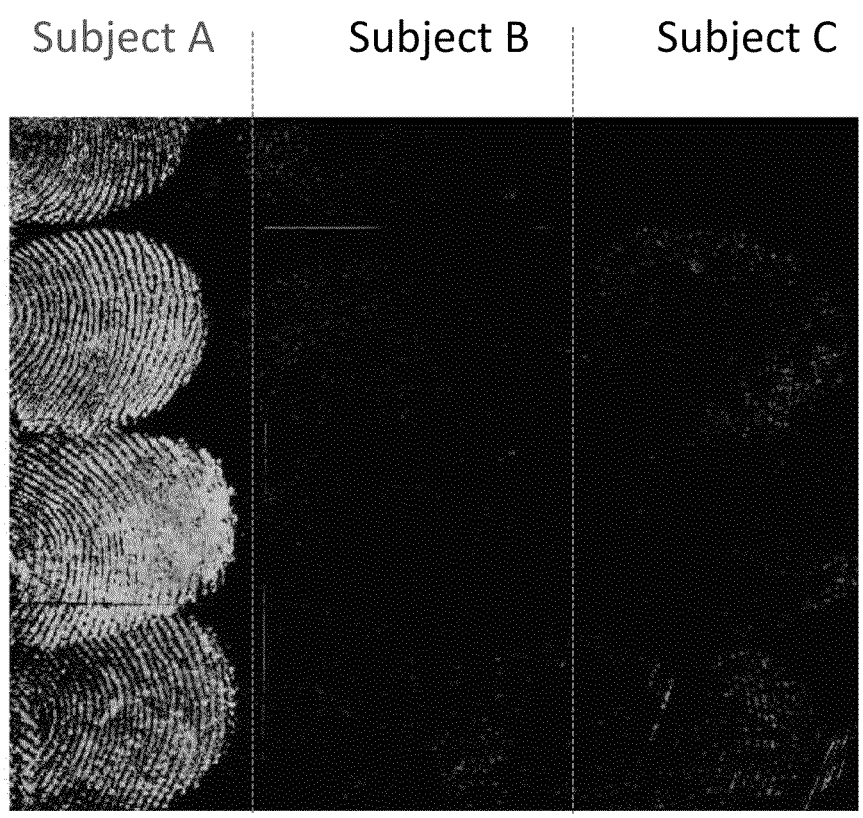
FIG. 1 shows reconstructed fingerprint images of acquired nanostructure-initiator mass spectrometry (NIMS) ion spectra from three subjects and demonstrates that Subject A was differentiated from Subjects B and C.

Conventional fingerprinting and biometrics are limited to providing an image of a fingerprint, but fail to capture and provide any chemical information present on the finger. As can be appreciated, a person's finger has latent chemical information that can help determine what a person has touched, where a person has been, and what chemicals or compounds a person has been exposed to. However, conventional fingerprinting and biometrics are incapable of harnessing this latent chemical information that is present on a person's finger.

Several embodiments provided herein relate to nanostructure-initiator mass spectrometry (NIMS) biometrics systems, assays and methods capable of providing both (1) a fingerprint image and (2) chemical information on the finger. In various embodiments, a method of generating a fingerprint image and chemical information from a subject's finger includes pressing the finger onto a NIMS chip surface so as to transfer analytes from the finger to the NIMS chip surface. The NIMS chip can then be analyzed to investigate the captured analytes by generating a mass spectrum at several positions on the NIMS chip surface, and reconstructing an image of the finger that not only provides a visual fingerprint but also a depth of chemical information on the analytes. Without being bound by theory, ionization of analytes on the NIMS chip surface by mass spectrometry can yield information that can be used to identify chemical signatures on the finger within the spatial image of the fingerprint thereby linking biometric signatures to a particular chemical composition.

The chemical information obtained from the fingerprint analysis can include, health, diet, microbiome, personal products (soaps etc), and other latent chemical contacts (explosives, plants, etc) all of which can be used to determine the history and physiology of the individual. In addition, ionization of analytes on the NIMS chip surface by mass spectrometry yields analyte-specific ions that can be used to reconstruct an image of the finger and identify the analyte itself.

The NIMS biometrics systems, assays and methods provided herein can find application in security and health industries. For example, in a security setting, the NIMS biometrics assays and methods described herein can provide a way of fingerprinting individuals and providing a depth of specific chemical information about the individuals including, for example, what they have touched, where they have been, and what they have been exposed to based on the analytes on their fingers.

For example, in a security setting, NIMS biometrics assays and methods described herein can be useful to detect or identify microbes, chemicals such as gunpowder and explosives, and endogenous markers present on individuals' fingers. This can be useful to help locate individuals of interest, link individuals to their past history, or detect specific compounds, such as explosives, drugs, and the like. In a health industry setting, the NIMS biometrics assays and methods described herein can provide a noninvasive test for specific analytes that are sweated or otherwise excreted into the skin. This can be useful for diagnosing the health status of the subject. Additionally, the NIMS biometric assays and methods described herein can be performed at different times on a subject, which can be useful for determining a physiological change in the subject over time such as a change in the subject's health status.

Some embodiments relate to systems for identifying the fingerprint of a subject. These systems may also be configured to identify particular analytes detected on the fingerprint taken from the subject. For example, one embodiment includes a system for identifying a subject that includes a nanostructure-initiator mass spectrometry (NIMS) chip connected to an electronic system configured to perform analysis on the captured NIMS data. For example, an analysis module may be running within the electronic system and be configured to read a fingerprint applied to the NIMS chip and determine a mass spectrum fingerprint pattern by the methods described herein. Once the mass spectrum pattern has been determined, a comparison module running in the electronic system is configured to compare the determined mass spectrum from the fingerprint to a database of known patterns in order to identify the subject. The system may also include an analyte detection module running in the electronic system and configured to read the mass spectrum fingerprint and identify analytes associated with the fingerprint. For example, analytes such as particular chemical, microbe, metabolite produced by the subject, endogenous biomarker, animal substance, ingested substance, or environmental substances may be identified.

In one embodiment, the analyte detection module can be configured by a processor to read the mass spectrum fingerprint and identify analytes associated with the fingerprint. The analyte detection module may also be configured to identify whether the analyte is a chemical, microbe, metabolite produced by the subject, endogenous biomarker, animal substance, ingested substance, or environmental substance. In addition, the analysis module in the system can be configured by a processor to determine a mass spectrum fingerprint by detecting ions derived from an analyte on the fingerprint. In this embodiment, the comparison module would be configured to identify the mass spectrum pattern unique to the subject by detecting a pattern of the ions derived from the analyte.

Skin Samples

Embodiments provided herein also relate to nanostructure-initiator mass spectrometry (NIMS) biometrics systems, assays and methods involving detection, identification, and/or imaging of analytes from an individual's skin. Any part of an individual's body having skin can be used in the NIMS biometrics assays and methods described herein. For example, skin samples can include samples of skin from one or more fingers, thumbs, palm, feet, lips, arms, legs, face, and/or any portion thereof. Various embodiments relate to generating an image of an individual's skin sample. For example, NIMS can be used to provide an image of an individual's fingerprint, thumbprint, palmprint, or footprint. Various embodiments relate to detecting and identifying analytes from an individual's skin sample. Accordingly, contemplated herein is any skin sample from an individual's body that can be useful for obtaining an image of the skin sample and/or chemical information about the skin sample via NIMS. In several embodiments, reconstructed images of acquired NIMS mass spectra can provide both an image of the skin sample and chemical information about the skin sample. It will be understood that in various embodiments described herein relating to fingerprinting or analyzing analytes present on a finger, corresponding embodiments for any other skin sample are contemplated and provided.

Nanostructure-Initiator Mass Spectrometry

In various embodiments, a fingerprint image and chemical information on a person's finger can be generated by nanostructure-initiator mass spectrometry (NIMS). NIMS is described in T. R. Northen, O. Yanes, M. T. Northen, D. Marrinucci, W. Uritboonthai, J. Apon, S. L. Golledge, A. Nordstrom, G. Siuzdak, *Nature* 2007, 449, 1033-1036; T. R. Northen, J. C. Lee, L. Hoang, J. Raymond, D. R. Hwang, S. M. Yannone, C. H. Wong, G. Siuzdak, *Proc. Natl. Acad. Sci. USA* 2008, 105, 3678-3683; and U.S. Patent Application Publication No. 2008/0128608, which are herein fully incorporated by reference. Production of NIMS chips is described in detail in H. K. Woo, T. R. Northen, O. Yanes, G. Siuzdak, *Nat. Protoc.* 2008, 3, 1341-1349, which is herein fully incorporated by reference.

A variety of apparatuses can be used in NIMS to determine analyte-specific ions corresponding to analytes present on a person's skin. For example, in several embodiments a time-of-flight mass analyzer is used for measuring the desorbed and ionized analyte. However, other non-limiting examples of mass analyzers that can be used include magnetic ion cyclotron resonance instruments, deflection instruments, and quadrupole mass analyzers.

By contacting a finger or other skin sample on an initiator-loaded substrate, such as a NIMS chip, thereby transferring analyte(s) to the substrate, the analyte-loaded substrate can be used for desorption and ionization of the analyte. In several embodiments, a NIMS substrate, such as a NIMS chip, is coated with a fluorous initiator, for example bis(heptadecafluoro-1,1,2,2-tetrahydrodecyl)tetramethyl-disiloxane. As used herein, the term "NIMS chip" is not limited to a particular shape or size and may be considered synonymous with the term "NIMS substrate," both terms referring to an initiator-loaded surface suitable for mass spectrometry. In some embodiments, the finger or skin sample does not directly contact the initiator-loaded substrate. In some embodiments, the fingerprint or the print of the skin sample is collected on another surface, for example a tape (e.g., a plastic tape or a gelatin tape), and then transferred onto the initiator-loaded substrate.

Because of its absorptivity, the NIMS chip can act as an energy receptacle. An irradiation source can provide energy that the substrate or initiator can absorb. The sources of irradiation can be electromagnetic radiation or ion beams. The electromagnetic radiation can be provided by a laser and results in a "laser-induced desorption." Alternatively, the initiator can be restructured by irradiation with an ion beam ("ion-induced desorption"). The irradiation source can be focused on the portion of the substrate containing the target. This absorbed radiation can be used to volatilize or rearrange (i.e., "restructure") an initiator. For example, the initiator can be volatilized when the initiator is turned into a gas or vapor. The volatilization or rearrangement of the initiator can be called "initiator restructuring." When the initiator is restructured, the analyte can be volatilized and ionized.

As one example, the laser radiation source can be an ultraviolet pulse laser. In some embodiments, 50 to about 500 laser shots from a 337 nm pulsed nitrogen laser (Laser Science, Inc.) with a power of 2 to 50 µJ/pulse can be used. Irradiation can be done with a lens, and with an optional neutral density filter; such methods of focusing and filtering laser radiation being known to those skilled in the art. An ion beam can be composed of positively charged clustered ions. A cluster source, such as $Bi_3^+$ ion source, can be used. Alternatively, other monoatomic and clustered ions can be used such as $Au^+$, $Ga^+$, and $Bi^+$.

The pressure during analyte desorption can vary substantially depending on the sensitivity desired. All pressure ranges at which MALDI-MS can operate are contemplated herein, as well as higher pressures similar to those in atmospheric MALDI (AP-MALDI). Lower pressures can be used to improve sensitivity and lessen interference problems. In certain embodiments, the pressures can be $10^{-6}$ to $10^{-7}$ torr. Higher reduced pressures can be used, up to atmospheric pressure, albeit with reduced instrumental sensitivity as the pressure rises. Reduced pressures lower than $10^{-7}$ torr can provide benefits to sensitivity and are contemplated herein. Current technology can readily achieve pressures as low as $10^{-1}$ torr.

In several embodiments, NIMS can provide an image of a finger or other suitable skin sample. For example, laser desorption/ionization mass spectrometry can be performed on a TOF/TOF mass analyzer system in positive reflector mode and a full mass spectrum ranging, for example, from about 50 to 2,000 m/z, can be recorded for every position at an x-y step-size of about 10 µm, 25 µm, 50 µm, 75 µm, 100 µm, 125 µm, 150 µm, 175 µm, 200 µm, 225 µm, or about 250 µm, or any size in between any of the aforementioned numbers.

Isotope Ratio Mass Spectrometry

In various embodiments, an analyte can be evaluated by isotope ratio mass spectrometry (IRMS). For example, the origin of an analyte can be determined by IRMS, which is capable of measuring the relative abundance or ratio of isotopes in an analyte. Such isotopes can be stable isotopes or radiogenic isotopes that decay over time and are commonly used in radiometric dating methods. A typical mass spectrum of ions might not provide sufficient information to determine the origin of an analyte, but IRMS can be used to measure the relative abundance of isotopes in the analyte or provide a ratio of isotopes in the analyte that is characteristic or indicative of the origin of the analyte. For example, IRMS can distinguish whether the analyte is from plant or petroleum material based on the abundance or ratio of isotopes in an analyte. By analogy, information on the isotope abundance or ratios in an analyte can be used to determine the origin of an analyte similar to carbon dating. In several embodiments, IRMS can be used to determine the abundance or ratios of isotopomers, which are isomers having the same number of each isotopic atom but differing in their positions. In various aspects, the ratio of isotopomers can be used to determine the origin of an analyte.

Image Reconstruction

Several embodiments provided herein relate to generating a skin sample image, such as a fingerprint image, by NIMS. Without being bound by theory, ionization of analytes on the NIMS chip surface by mass spectrometry yields analyte-specific ions that can be used to reconstruct an image of the skin sample. This can be performed computationally, for example, by reading each generated mass spectrum on the NIMS chip and storing the intensity information of each mass spectrum in a 2D array, wherein the first dimension represents the pixels and the second dimension represents the mass-to-charge (m/z) values of each mass spectrum. For example, to integrate multiple 2D images and conduct statistical analysis, a script can be made in the MATLAB (The MathWorks; Natick, Mass.) programming language and a script can be made to import imaging data. A script can be made to read the mass spectra at each spatial coordinate of each 2D section and store the intensity information in a 2D sparse array. In various embodiments, reconstructed images can provide chemical information from a subject's finger in addition to a visual image of a fingerprint.

Analytes

Several embodiments provided herein are drawn to identifying, determining, or detecting an analyte on a subject's skin sample (e.g. finger) by NIMS. Without limitation, any kind of analyte suitable for NIMS can be identified, determined, or detected in the present embodiments. The identification, determination, or detection of an analyte on a subject's skin sample by NIMS biometrics assays and methods provided herein can be useful for determining what a person has touched or where a person has been. This is particularly the case when a specifically detected analyte is native or indicative of a particular geographic location or unique to a specific item that a person may have been exposed to.

In various embodiments, an analyte is identified, detected, or determined by contact a subject's skin to a NIMS chip, thereby applying the analyte to the NIMS chip. Next, mass spectra can be acquired from the chip and the identity of the analyte can be determined based on ions specific to the analyte. In some aspects, the identity of the analyte can be determined by comparing the detected analyte-specific ions, or reconstructed images thereof, with known or predetermined analyte-specific standard ions or patterns/profiles of ions, or reconstructed images thereof. In some aspects, the identity of the analyte can be determined based on a mass spectrum profile of ions, which need not be analyte-specific. In such aspects, the identity of the analyte can be determined by comparing and matching a profile of ions from the analyte with a known or predetermined profile.

One class of analytes suitable for NIMS identification, determination, or detection includes chemicals. In the context of the security industry, non-limiting examples of chemicals suitable for NIMS biometrics analysis include gunpowder, explosives, or drugs (recreational, prescription, contraband, etc.).

1. Gunpowder and Explosives

Examples of gunpowder or explosives that can be identified, determined, or detected in several embodiments include, but are not limited to, organic compounds containing $-NO_2$, $-ONO_2$ and $-NHNO_2$ groups. This includes compounds such as nitroglycerin, TNT, HMX, PETN, nitrocellulose, acetone peroxide, RDX, C-4 and "black powder". Examples of black powder include potassium nitrate, charcoal and sulfur. In addition, flash powder such as a fine metal powder having aluminum or magnesium, and a strong oxidizer is contemplated. This would include potassium chlorate or perchlorate and ammonium nitrate and aluminum powder. Other detectable substances include Armstrong's mixture (potassium chlorate and red phosphorus), Sprengel explosives (any strong oxidizer and highly reactive fuel), ANFO (ammonium nitrate and fuel oil), cheddites (chlorates or perchlorates and oil), oxyliquits (mixtures of organic materials and liquid oxygen), panclastites (organic materials and dinitrogen tetroxide), ammonium permanganate, azo-clathrates, copper acetylide, diazodinitrophenol, hexamethylene triperoxide diamine, lead azide, lead styphnate, lead picrate, mercury(II) fulminate, nitrogen trichloride, nitrogen triiodide, silver azide, silver acetylide, silver fulminate, sodium azide tetrazine, tetraamine copper complexes, and tetrazoles.

2. Drugs

As referred to herein, "drugs" are any chemical substances capable of effecting a physical, mental, emotional, or behavioral change in an individual. Examples of drugs that can be that can be identified, determined, or detected in several embodiments include but are not limited to the following drug categories: narcotics, stimulants, depressants (sedatives), hallucinogens, and cannabis. These categories include drugs legally produced and prescribed by doctors as well as those illegally produced and sold outside of medical channels.

Cannabis sativa is the common hemp plant. When ingested, this plant causes hallucinogens with some sedative properties, and includes marijuana, tetrahydrocannabinol, hashish, and hashish oil. Other drugs, such as cocaine, chloral hydrate, barbiturates, benzodiazepines, methaqualone, glutethimide, and others may be detected using the systems and methods described herein.

Hallucinogens such as LSD, mescaline and peyote, amphetamine variants phencyclidine, phencyclidine analogues, and others can also be detected. In addition, hashish, methaqualone, opium, opium derivatives, morphine, codeine, heroin, and other drugs may be detected using the systems and methods described herein.

Any of the aforementioned drug categories and examples therein can be suitable analytes for NIMS biometrics assays and methods provided herein.

3. Microbes

As referred to herein, "microbes" are unicellular or multicellular microorganisms that live alone or in a colony. Examples of microbes that can be that can be identified, determined, or detected in several embodiments include but are not limited to bacteria, fungi, archaea, protists, microscopic plants (green algae), animals such as plankton and the planarian, and viruses.

In various embodiments, NIMS biometrics assays and methods can include identifying a community of microbes on an individual's skin. For example, a subject having a community of microbes on the finger can contact the finger to a NIMS chip, thereby applying the community of microbes to the NIMS chip. Next, mass spectra can be acquired from the chip and the identity of the community of microbes can be determined based on ions specific to the community of microbes. In some aspects, the identity of the community of microbes can be determined by comparing the detected ions (or reconstructed images thereof) with known ion standards or ion patterns/profiles (or reconstructed images thereof).

Likewise, in several embodiments the identity of an individual can be determined based on the identification of a community of microbes. For example, an unknown individual of interest having a particular community of microbes can be positively identified by screening for persons with NIMS biometric assays and methods provided herein. In other words, NIMS biometrics assays and methods can be used to match an individual with a signature community of microbes.

Furthermore, in several embodiments the origin of a subject's exposure can be determined based on the identification of a microbe by NIMS biometric assays and methods provided herein. For example, if an individual is determined to have been exposed to a microbe based on the NIMS mass spectra or reconstructed image thereof (e.g. fingerprint), the identity of the microbe determined by detecting the microbe-specific ion(s) can indicate where the individual got exposed to the microbe, particularly if the microbe is native to a certain geographic region.

4. Additional Analytes

Other suitable analytes can include an animal substance to indicate whether an individual has been in contact with a particular animal, an ingested substance, or an environmental substance such as soil, dirt, mud, or plants, which can be useful in determining where an individual has been or what an individual has been exposed to.

Moreover, the analytes suitable for NIMS biometrics assays and methods provided herein are not limited to exogenous substances, but can also include a metabolite produced by an individual or an endogenous biomarker. Accordingly, individuals can be distinguished based on individual-specific NIMS ions and fingerprints. Various embodiments are drawn to use of NIMS biometrics to differentiate individuals.

Determining and Diagnosing Physiological Changes

The NIMS biometrics assays and methods provided herein can also be used to determine a physiological change in an individual by comparing NIMS mass spectra or reconstructed images thereof (e.g. fingerprints) obtained at different times. For example, an individual can touch a NIMS chip, thereby applying suitable analytes to the NIMS chip, at various time intervals. A NIMS biometrics pattern or profile reflective of a physiological change in the individual that occurred over time can be obtained. For example, a difference in the acquired NIMS mass spectra or images thereof (e.g. fingerprints) between time intervals indicates that an individual underwent a physiological change.

In several aspects, the physiological change is a health status change in the individual. For example, an individual at a first time point can touch a NIMS chip before exercising. The individual can then touch a NIMS chip at a later time point after exercising. The difference in the acquired NIMS mass spectra or reconstructed images thereof (e.g. fingerprints) before and after exercise can provide a biometrics pattern or profile of exercise.

Likewise, in several embodiments, the health status of an individual can be diagnosed by matching an individual's acquired NIMS mass spectra or reconstructed images thereof (e.g. fingerprints) with predetermined NIMS mass spectra or reconstructed images thereof (e.g. fingerprints) corresponding to a known health status. For example, a predetermined biometrics pattern indicative of exercise can be matched against an individual's biometrics pattern or profile to determine if the individual has exercised.

Any health status that can change over time is contemplated in the present embodiments. Examples of suitable health status conditions for NIMS biometrics determination and/or diagnosis include but are not limited to hygiene, such as washing hands, disease progression (e.g. infection), recovery from disease, diet and nutrition, exercise, response to medication, fatigue, sleep deprivation, substance addiction, and the like.

NIMS biometrics assays and methods disclosed herein can be used for various applications including a dynamic assessment of change in chemical composition of an individual over time, comparison of the chemical composition of one individual to other(s), and detection of change(s) in the spatial arrangement of compounds on the skin.

The above description discloses several systems, methods and materials relating to the present invention. This invention is susceptible to modifications that will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention. All references cited herein are incorporated by reference in their entirety and are hereby made a part of this specification

EXAMPLES

Having generally described embodiments of the present invention, a further understanding can be obtained by reference to certain specific examples which are provided herein for purposes of illustration only, and are not intended to be limiting.

Example 1

Nanostructure-Initiator Mass Spectrometry (NIMS)

Fabrication of NIMS Chips.

NIMS chips for biometrics were made and coated as described previously. In addition, the same initiator was used for fingerprint imaging under each tested conditions and was fluorous phase as described previously (Northen et al., "Clathrate Nanostructures for Mass Spectrometry," Nature (2007) 449, 1033-1036; Woo et al., "Nanostructure-Initiator Mass Spectrometry (NIMS): A protocol for preparing and applying NIMS surfaces for high sensitivity mass analysis,". Nature Protocols (2008) 3, 1341-1349), each of which is incorporated by reference in its entirety.

Briefly, a 4" silicon wafer (single-sided polished P/Boron, orientation <1-0-0>, resistivity 0.01-0.02 Ωcm, thickness 525±25 μm) obtained from Silicon Quest International (Santa Clara, Calif.) was cut into a 70×70 mm square and cleaned thoroughly with methanol, followed by anodic etching with 25% hydrofluoric acid in ethanol in a custom made Teflon etching chamber using extreme caution. A current of 2.4 A was applied for 15 minutes. After etching, chips were coated by adding 400 μL of the initiator liquid bis(heptadecafluoro-1,1,2,2-tetrahydrodecyl)tetramethyl-disiloxane (Gelest; Morrisville, Pa.) for 20 minutes. Excess initiator was blown off with nitrogen.

Imaging Mass Spectrometry.

Laser desorption/ionization mass spectrometry was performed on a 5800 TOF/TOF mass analyzer system (AB Sciex; Foster City, Calif.) in positive reflector mode. The third harmonic of a Nd:YAG laser (355 nm) was used at a repetition rate of 200 Hz with 25 shots per spot. A full mass spectrum ranging from 50 to 2,000 m/z was recorded for every position at an x-y step-size of 75 μm. All samples were imaged with identical settings. Imaging data was stored in the Analyze 7.5 data format (Mayo Foundation; Rochester, Minn.).

Image Reconstruction and Statistical Analysis.

The following steps were used to integrate multiple 2D images, subsequently followed by statistical analysis. All steps were performed using custom made scripts in the MATLAB (The MathWorks; Natick, Mass.) programming language.

Import of Imaging Data.

A custom script was used to parse the Analyze 7.5 image files. The script read the spectra at each spatial coordinate of each 2D section and stored the intensity information in a 2D sparse array. The first dimension represents all the pixels, and the second dimension represents all the m/z values.

Total Spectrum and Peak Finding.

The major ions in the data stack were determined with the help of an integrated spectrum, whereas a defined m/z axis from 50 to 2,000 in steps of 0.01 was chosen as the basis for registering all of the acquired spectra. After smoothing the total spectrum with a Gaussian point-spread function with a 0.2 Da standard deviation, the top peaks in this spectrum were selected to represent the major ions in the data stack. All m/z values in each pixel were binned +/−0.3 Da to compensate for any shifts in m/z that occurred over the imaging run.

Multivariate Statistical Analysis.

Non-negative matrix factorization (NMF) was used for the multivariate analysis. First, using the multiplicative update algorithm, twenty replicates were performed from random starting values. The best of these parameters was then used as the initial guess where the alternating least squares algorithm was used. The non-negative factors, W and H, were used to represent regions of the data in a reduced dimension. W can be reshaped into a (x,y, factors) matrix for visualization and analysis. H is the loadings matrix that shows the contribution of each of the ions towards each of the factors.

Subjects.

The subjects were healthy Caucasian young adults, males and females, aged 25-45 years old. One male and one female subject were part of the same household indicating/providing a highly similar background environmental exposure.

NIMS Printing.

All NIMS fingerprinting were performed at the exact same location, in the same room, in the laboratory. After printing, the NIMS chip was not moved or manipulated until being placed for scanning in the ABI5800 machine. The individuals practiced NIMS fingerprinting the day before on a training chip, by pressing left and right fingers on the surface chip for 5 seconds. Control fingerprints: controls were taken at three different times over the course of 3 months, to check for intra individual stability.

Example 2

Differentiation of Individuals by NIMS Fingerprints

NIMS fingerprints were obtained from 3 individuals (Subjects A-C) by applying one finger at a time for 5 seconds. No pre-processing, fixative, or chemical was used on the fingers prior to printing. All fingers were printed consecutively. Subjects A-C printed their fingers upon arrival in the laboratory without washing their hands in order to include their baseline personal and environmental exposure.

Figure 2:
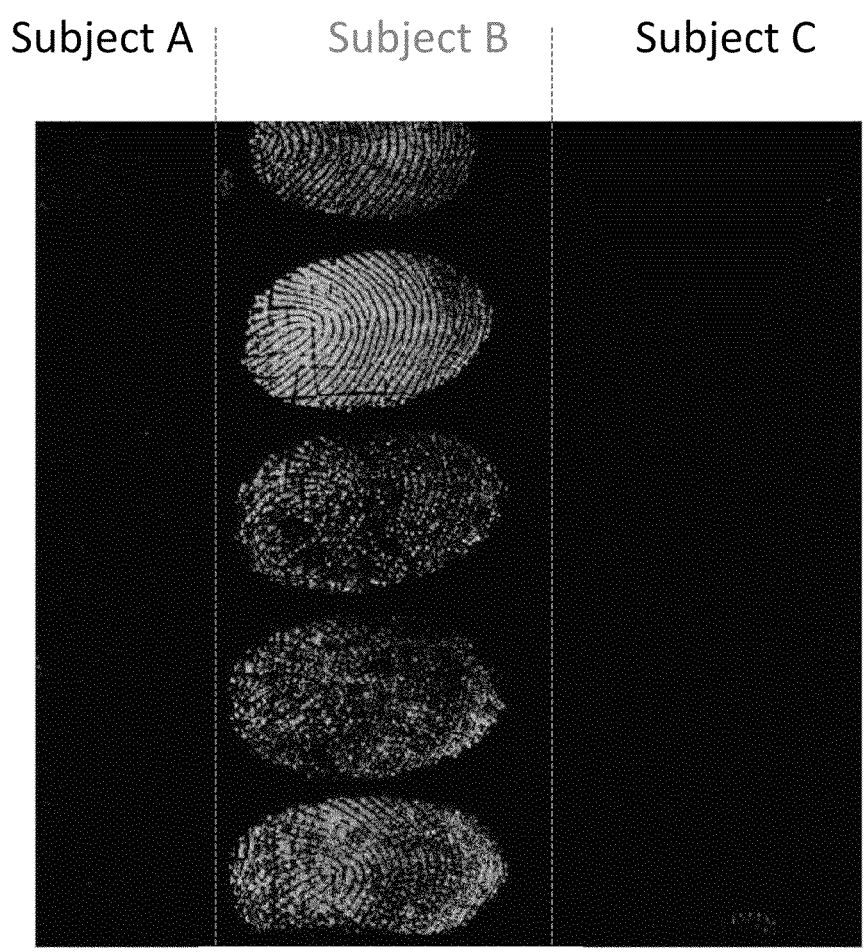
FIG. 2 shows reconstructed fingerprint images of acquired nanostructure-initiator mass spectrometry (NIMS) ion spectra from three subjects and demonstrates that Subject B was differentiated from Subjects A and C.

As shown in FIG. 1, Subject A was differentiated from Subjects B and C based on the ions detected on the fingers using NIMS biometrics. Similarly, as shown in FIG. 2, Subject B was differentiated from Subjects A and C based on the ions detected on the fingers using NIMS biometrics.

Figure 3:
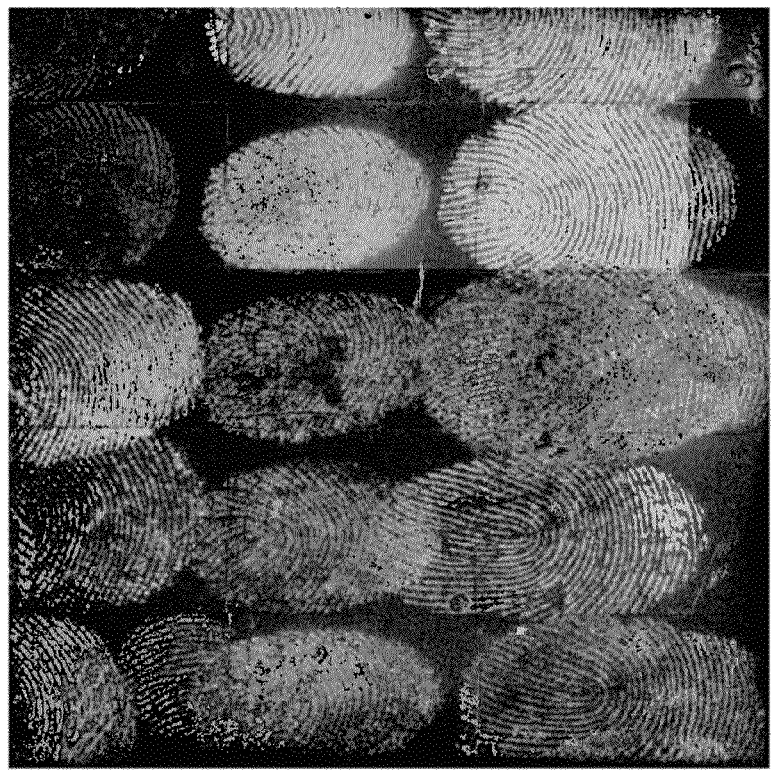
FIG. 3 shows reconstructed fingerprint images of acquired nanostructure-initiator mass spectrometry (NIMS) ion spectra from different healthy subjects and demonstrates that human beings share similar ions on their fingers.

Different individuals were also found to share similar ions on their fingers. As shown in FIG. 3, NIMS fingerprints from different healthy adults showed similar ions detected on the fingers using NIMS biometrics.

These data collectively show that individuals can be differentiated by NIMS fingerprinting based on specific ions detected on the fingers using NIMS biometrics. However, individuals also share certain similar ions.

Example 3

Distinguishing Fingers from the Same Individual

Figure 4:
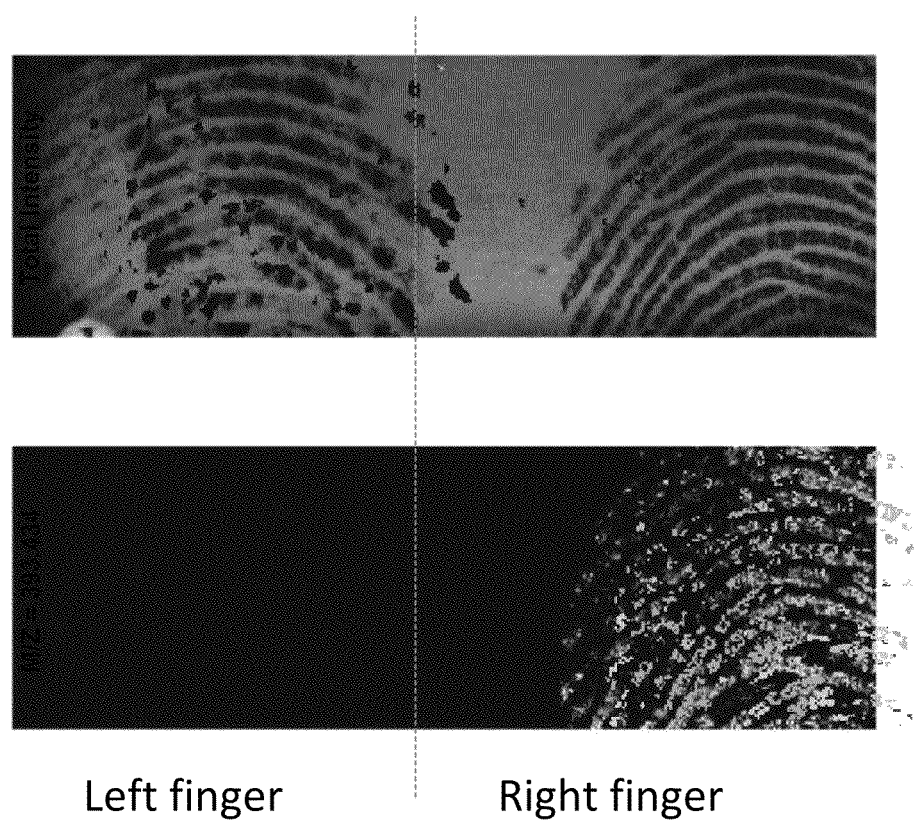
FIG. 4 shows reconstructed fingerprint images of acquired nanostructure-initiator mass spectrometry (NIMS) ion spectra from a subject's left finger and right finger. The fingerprint images show detection of an ion specific to the right finger of the subject.

NIMS fingerprints were obtained from a subject's left finger and right finger at the same time. No preprocessing, fixative, or chemical was used on the fingers prior to printing. As shown in FIG. 4, the subject's right finger had a specific ion distinguishable from the left finger. The total intensity of the print from the left and right finger was visualized as a control and found to be comparable. These data indicate that different fingers from the same individual have distinguishable specific ions and can be detected by NIMS biometrics.

Example 4

Detection of Environmental Exposure

Plant

NIMS fingerprints were obtained from 3 individuals (Subjects A-C). Subjects A and B did not touch a plant before fingerprinting. Subject C provided a fingerprint before and after touching a plant for 5 seconds. Fingerprinting on the chip was performed within 5 minutes after touching the plant, without touching anything in between.

Figure 5:
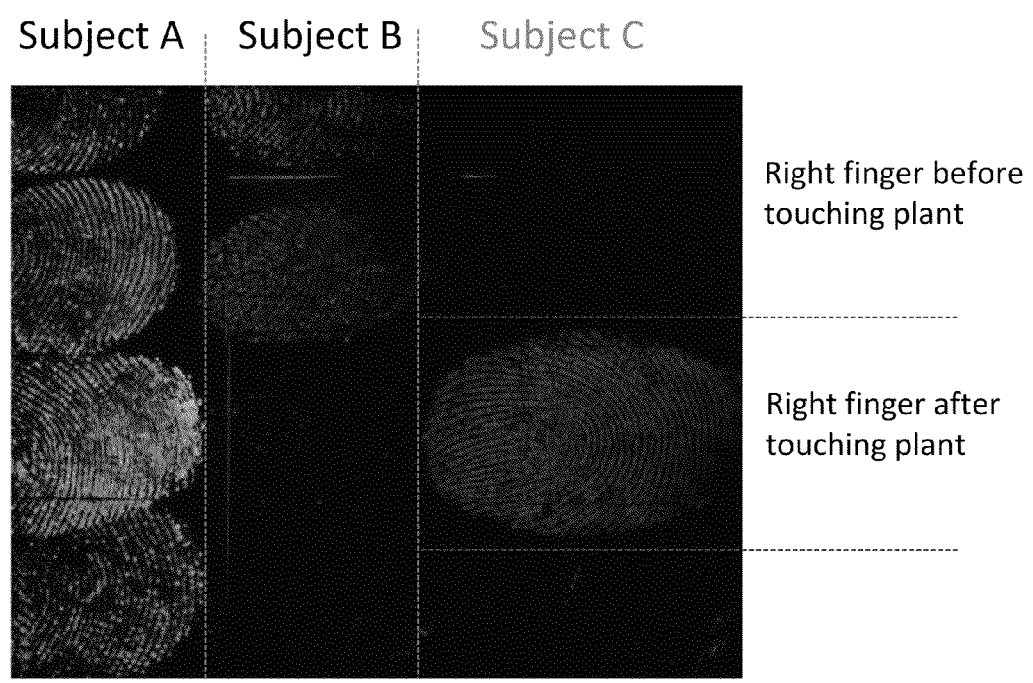
FIG. 5 shows reconstructed fingerprint images of acquired nanostructure-initiator mass spectrometry (NIMS) ion spectra from three subjects and demonstrates that an ion specific to Subject C after touching a plant was detected.

As shown in FIG. 5, an ion specific to Subject C after touching a plant was detected and imaged. These data indicate that an individual who touched a plant can be differentiated from other individuals, and that an individual's fingerprint can be differentiated before and after touching an environmental substance such as a plant.

Example 5

Detection of Environmental Exposure

Soil Dirt

NIMS fingerprints were obtained from a subject. The subject provided fingerprints before and after touching soil dirt for 5 seconds. Fingerprinting on the chip was performed within 5 minutes after touching soil dirt, without touching anything in between.

Figure 6:
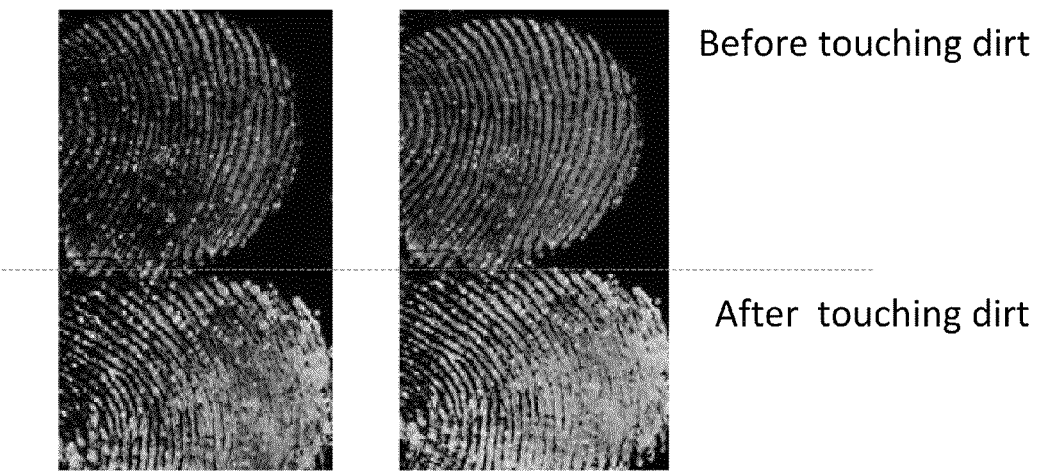
FIG. 6 shows reconstructed fingerprint images of acquired nanostructure-initiator mass spectrometry (NIMS) ion spectra from a subject before and after touching soil dirt, and demonstrates that an ions specific to the subject after touching soil dirt was detected.

As shown in FIG. 6, ions specific of the subject after touching a plant were detected and imaged. These data indicate that an individual who touched soil dirt can be differentiated from other individuals, and that an individual's fingerprint can be differentiated before and after touching an environmental substance such as soil dirt, based on NIMS ions profiles.

Example 6

Detection of Environmental Exposure

Mud

NIMS fingerprints were obtained from a subject. The subject provided a fingerprint before and after touching mud for 5 seconds. Fingerprinting on the chip was performed within 5 minutes after touching mud, without touching anything in between.

Figure 7:
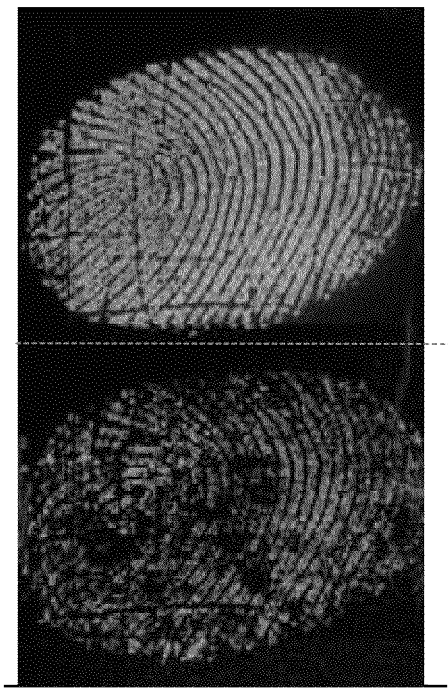
FIG. 7 shows reconstructed fingerprint images of acquired nanostructure-initiator mass spectrometry (NIMS) ion spectra from a subject before and after touching mud, and demonstrates that an ions differing before and after touching mud were detected.

As shown in FIG. 7, ions differing before and after touching mud were detected and imaged. These data indicate that an individual who touched mud can be differentiated from other individuals, and that an individual's fingerprint can be differentiated before and after touching an environmental substance such as mud, based on NIMS ions profiles.

Example 7

Differentiation of Environmental Exposure Based in NIMS Ions Profiles

Figure 8:
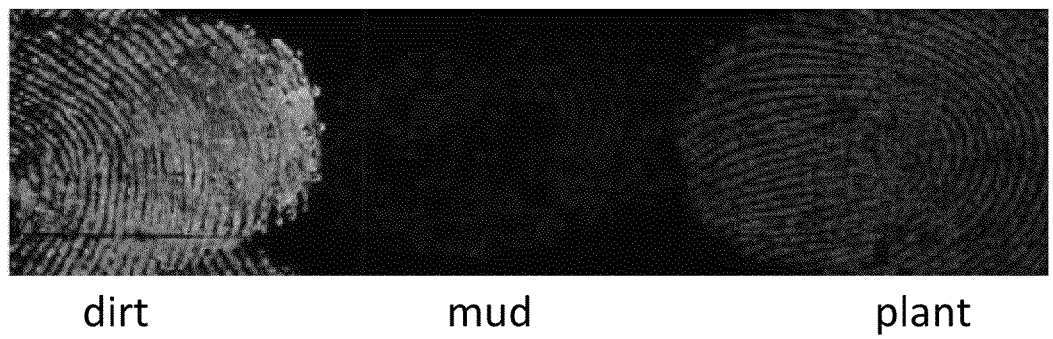
FIG. 8 shows reconstructed fingerprint images of acquired nanostructure-initiator mass spectrometry (NIMS) ion spectra from touching dirt, mud, or a plant, and demonstrates that different ions are specific to soil, dirt, and mud.

The data from Examples 4-6 were compared. As shown in FIG. 8, the data demonstrated that different ions are specific to soil dirt, mud, and plant. The data indicate that environmental exposure can be differentiated based on NIMS ions profiles.

Example 8

Detection of Chemical Exposure

Gun Powder

Figure 9:
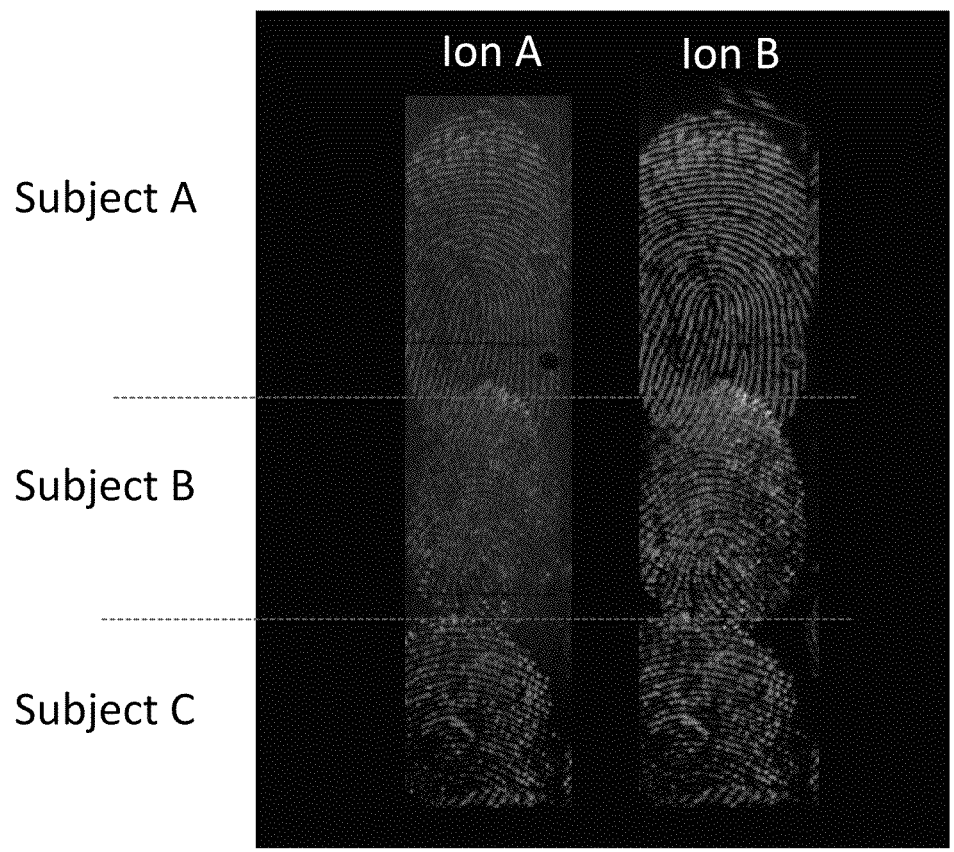
FIG. 9 shows reconstructed fingerprint images of acquired nanostructure-initiator mass spectrometry (NIMS) ion spectra from three subjects who each touched gunpowder and demonstrates that ions specific to gunpowder were detected.

NIMS fingerprints were obtained from 3 individuals (Subjects A-C) who each touched gunpowder for 2 seconds or less. Fingerprinting on the chip was performed within 5 minutes after touching gunpowder, without touching anything else. As shown in FIG. 9, ions specific to the presence of gunpowder on the fingers of the subjects were detected and imaged. These data indicate that an individual who touched gunpowder can be differentiated from other individuals, and that an individual's fingerprint can be differentiated before and after touching a chemical substance such as gunpowder, based on NIMS ions profiles.

Example 9

Detection of Health Status

Dirty Hands

Figure 10:
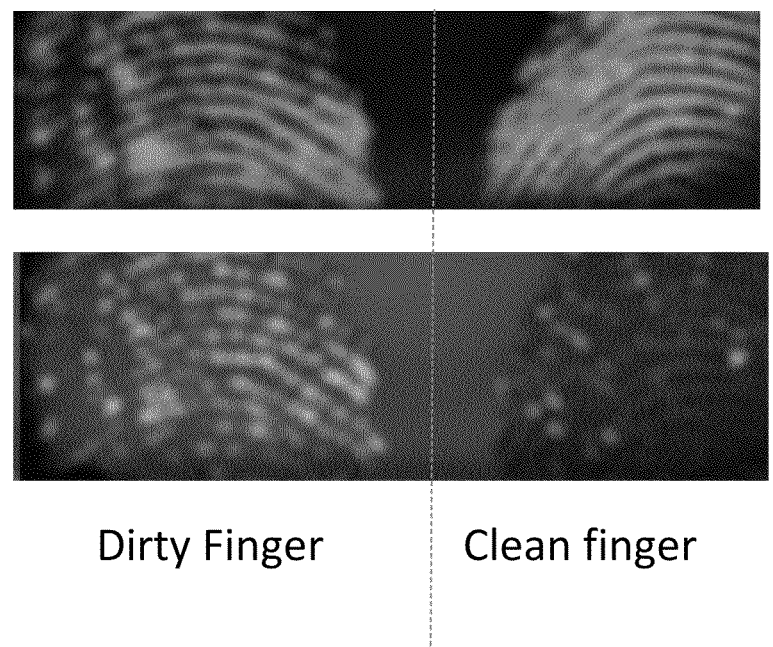
FIG. 10 shows reconstructed fingerprint images of acquired nanostructure-initiator mass spectrometry (NIMS) ion spectra from clean and dirty fingers and demonstrates that ion differences between clean and dirty fingers were detected.

Subjects washed both hands in the laboratory for 30 seconds. After rinsing hands without using any paper tissue or drying method, subjects waited for 2.5 hours before printing onto the chip. During this time, each subject was asked to perform normal daily activities. After 2.5 hours, the subjects were asked to wash only one finger. After rinsing, subjects did not use any tissue. In FIG. 10, the fingerprinting of the two fingers, "dirty" and "clean" was performed within 5 minutes, the two fingers printed next to each other on the chip.

As shown in FIG. 10, ion differences between a dirty finger and a finger washed with hand soap were detected and imaged. These data indicate that the health status of an individual, such as hygiene, can be determined based on NIMS ions profiles.

Example 10

Detection of Health Status

Exercise

Subjects were asked to perform moderate exercise in order to increase their cardiac heart rate without reaching exhaustion. For this given experiment, individuals hiked a moderate hill for approximately 15 minutes and walked down the same hill for approximately 5 minutes. Fingerprinting on the chip was performed in the laboratory within 5 minutes, without touching any items.

Figure 11:
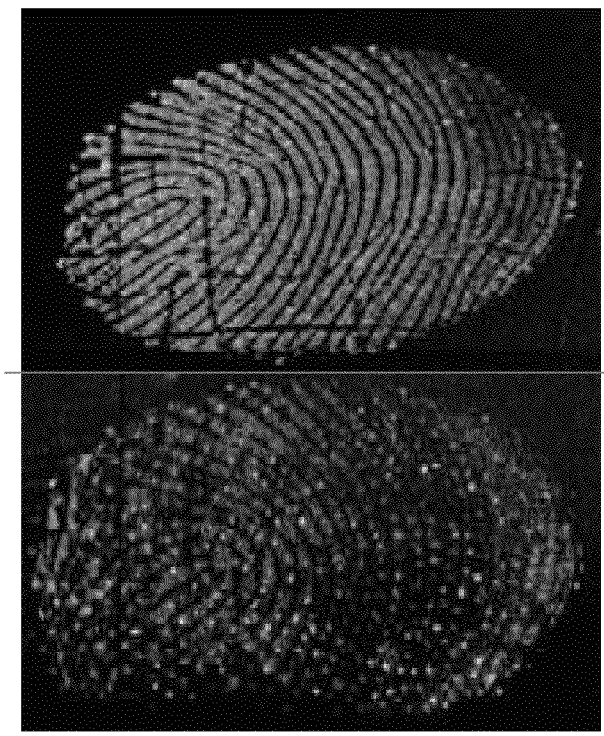
FIG. 11 shows reconstructed fingerprint images of acquired nanostructure-initiator mass spectrometry (NIMS) ion spectra from a subject before and after exercising, and demonstrates that ions different before and after exercise were detected.

As shown in FIG. 11, ions different before and after a person exercised for 20 minutes were detected and imaged. The ions on the skin had fine spatial location. These data indicate that the health status of an individual, such as exercise, can be determined based on NIMS ions profiles.

Example 11

Chemical Analysis by Skin Touch

Mass Spectrometry Imaging (CAST-MSI)

This example illustrates a non-limiting process by which raw data obtained by skin touch is transformed into chemical and image information. The process includes various steps, for example, 1) acquisition of raw data; 2) integration of retrospective analyses; 3) processing of raw spectra; 4) statistical analysis; and 5) reconstruction of this information into the representation of an image.

Figure 12:
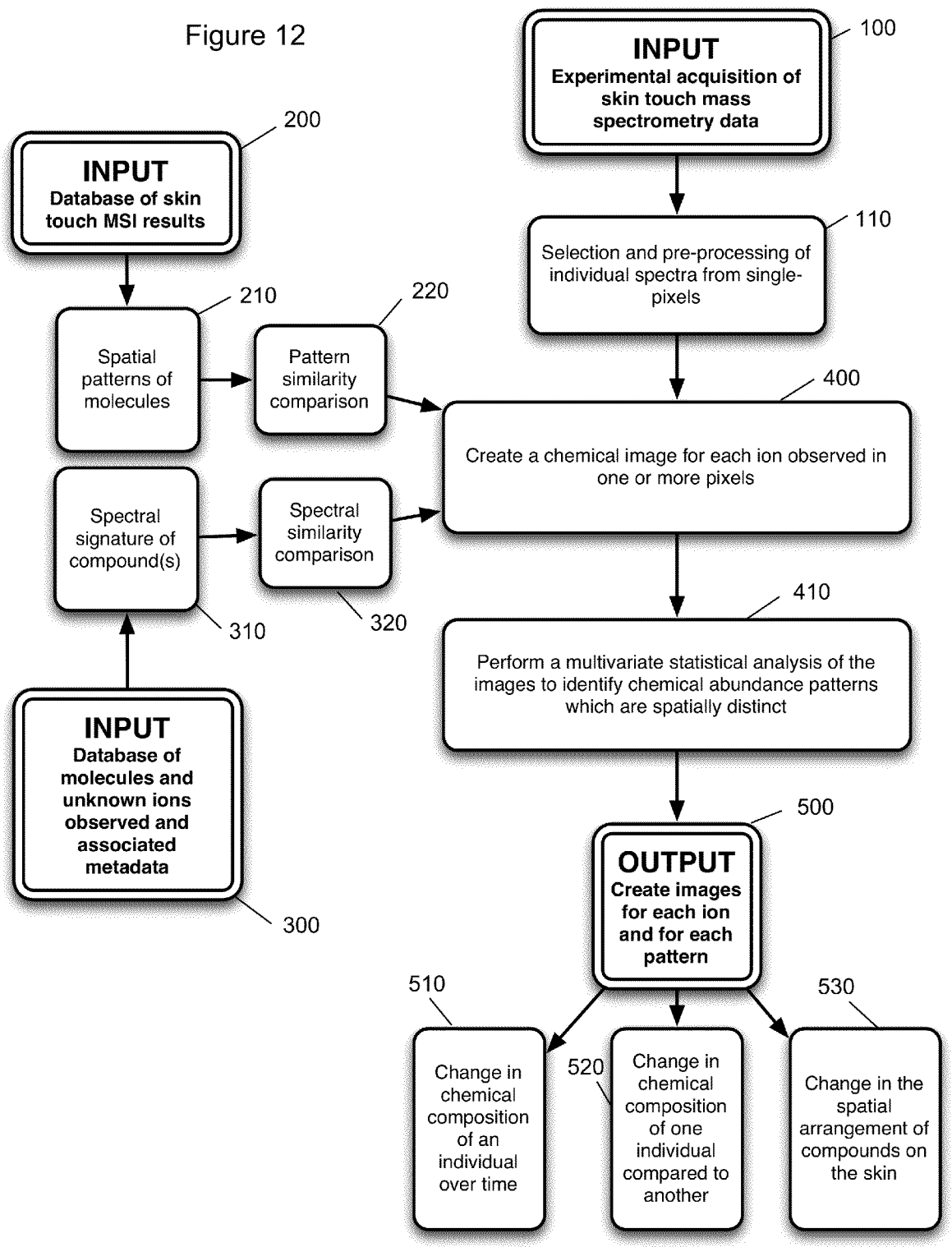
FIG. 12 depicts an illustrative embodiment of a process for chemical analysis by skin touch: mass spectrometry imaging (CAST-MSI) within the scope of the present disclosure.

FIG. 12 depicts an illustrative embodiment of the process. At block 100, chemical images of the molecules present on an individual's skin is built and used as input. In the process, three databases are used: 1) at block 100, a data base is built using the experimental acquisition of skin touch mass spectrometry image (MSI) data; (2) at block 200, a database of previous skin touch MSI results is provided; and (3) at block 300, a database of characteristics of molecules and unknown ions observed and associated metadata is built and provided. At block 400, the data from the three databases are then integrated to generate images for each ion observed in one or more pixels and for each chemical abundance pattern identified.

Block 100 can be followed by block 110. At block 110 (Selection and preprocessing of individual spectra from single-pixel), the primary input to the workflow is the experimentally acquired skin touch mass spectrometry image (MSI) data set. The data set contains a mass spectrum for every pixel recorded. Specific preprocessing steps of each spectrum include background subtraction, smoothing of the spectra, and peak finding. These preprocessing steps aid in denoising the raw data to better identify meaningful signals and to more accurately quantify their relative abundance.

Block 200 is followed by block 210. At block 210 (Spatial pattern of molecules), referencing datasets containing previous skin touch MSI results and derived data products enables the capability to detect and determine treatments, timepoints, and conditions that a subject may have experienced. Findings are extracted from archival data including specific ions and their spatial organization. These ions and spatial patterns can be compared to the current dataset being considered for analysis. To facilitate these operations, archival information of position and identification for the current dataset can be stored for future use.

Block 210 is then followed by block 220. At block 220 (Pattern similarity comparison), pre-existing spatial patterns are compared to the patterns observed in the current image by convolution based pattern matching algorithms. Patterns in the current image under consideration are expected to have high similarity-scores with patterns that exhibit the same spatial distribution.

Block 300 is then followed by block 310. At block 310 (Spectral signature of compounds), analyte-specific ion patterns/profiles are obtained and the identity of the analyze can be determined. A pure compound when desorbed, ionized, and detected by mass spectrometry typically is represented by more than one unique ion. The multitude of peaks can include isotopes, adducts formed by various ionization mechanisms, degradation products, and other adducts. Consequently, a unique ion is rarely used for identification purposes. However, in mass spectrometry, there are often unique ions that indicate the presence or absence of a class of molecules. The identity of the analyte can be determined by comparing the detected analyte-specific ions, or reconstructed images, with known or predetermined analyte-specific standard ions or patterns/profiles of ions, or reconstructed images. The identity of the analyte can also be determined by comparing and matching a profile of ions from the analyte with a known or predetermined profile.

Block 310 is followed by block 320. At block 320 (Spectral similarity comparison), spectral pattern matching is performed. A wide variety of strategies can be used to perform the spectral pattern matching, for example, the use a correlation score based on peaks that have matching m/z within a narrowly defined range. By using this approach, a pattern is considered matching if it has both the same set of peaks and relative intensity values within a range required for distinguishing between known molecules or unknown molecules.

At block 400 (Create a chemical image for each ion observed in one or more pixels), an integration step is performed. This step integrates the results from boxes 220 and 320 to generate the chemical image for each ion, know or unknown.

At block 400, for each ion observed in the MSI image, the intensity of that ion across all spatial locations is computed based on the pattern similarity comparison of skin touch MSI results obtained at box 220 and the spectral similarity comparison of known molecules obtained at box 320. The values obtained represent an image of the ion in two spatial dimensions. Various approaches can be used to compute this image, for example, determining the sum of the ion's intensity about a narrowly defined m/z range; determining the max intensity about a narrowly defined m/z range; or determining a peak height or area identified by a peak finding strategy within the same m/z range.

Block 400 is followed by block 410. At block 410 (Identification of spatially distinct chemical abundance patterns from the image), a multivariate statistical analysis can be used to identify spatial patterns that have similar spectra. Various analysis methods can also be used to identify the primary spectral patterns which comprise the dataset, including principle component analysis (PCA), non-negative matrix factorization (NMF), and k-means clustering.

Block 400 is followed by block 500. At block 500 (CAST-MSI Output: obtain images for each ion and each pattern), a fingerprint image is reconstructed from the mass spectra generated at sites on the NIMS chip contacted with a finger. Raw and processed data is converted into files in commonly used image formats, for example jpg, tiff, and png format files.

The chemical biometrics generated at block 500 can be used in a wide variety of applications, for example, they can be used to link individuals to their actions based on the chemical composition of their fingerprints. For example, block 500 can be followed by one or more of blocks 510, 520, 530. At block 510, change in chemical composition or skin of an individual over time is determined. At block 520, change in chemical composition or skin of one individual is compared to another individual. At block 530, change in the spatial arrangement of compounds on the skin of an individual is determined. At one or more of blocks 510, 520, 530, the chemical composition can include presence of specific microbial lipids from geographically defined microbial strains, contact with chemicals including explosives, diets etc.

It should be realized that the invention is operational with numerous other general purpose or special purpose computing system environments or configurations. Examples of well-known computing systems, environments, and/or configurations that may be suitable for use with the invention include, but are not limited to, personal computers, server computers, hand-held or laptop devices, multiprocessor systems, microprocessor-based systems, programmable consumer electronics, tablets, network PCs, minicomputers, mainframe computers, distributed computing environments that include any of the above systems or devices, and the like.

As used herein, instructions refer to computer-implemented steps for processing information in the system. Instructions can be implemented in software, firmware or hardware and include any type of programmed step undertaken by components of the system.

The system may be comprised of various modules as discussed herein. As can be appreciated by one of ordinary skill in the art, each of the modules comprises various sub-routines, procedures, definitional statements and macros. Each of the modules are typically separately compiled and linked into a single executable program. Therefore, the following description of each of the modules is used for convenience to describe the functionality of the preferred system. Thus, the processes that are undergone by each of the modules may be arbitrarily redistributed to one of the other modules, combined together in a single module, or made available in, for example, a shareable dynamic link library.

The system may be written in any conventional programming language such as C, C++, BASIC, or Java, and ran under a conventional operating system. C, C++, BASIC and Java are industry standard programming languages for which many commercial compilers can be used to create executable code.

The invention disclosed herein may be implemented as a method, apparatus, or article of manufacture using standard programming or engineering techniques to produce software, firmware, hardware, or any combination thereof. The term "article of manufacture" as used herein refers to code or logic implemented in hardware or computer readable media such as optical storage devices, and volatile or non-volatile memory devices. Such hardware may include, but is not limited to, field programmable gate arrays (FPGAs), application-specific integrated circuits (ASICs), complex programmable logic devices (CPLDs), programmable logic arrays (PLAs), microprocessors, or other similar processing devices.

What is claimed is:

1. A method of identifying a subject comprising:
generating a mass spectrum from a nanostructure-initiator mass spectrometry (NIMS) chip, wherein the chip comprises an analyte from the subject's skin;
identifying a mass spectrum pattern unique to the subject;
comparing the mass spectrum pattern to a known pattern, thereby identifying the subject;
wherein generating the mass spectrum comprises contacting the subject's skin to the NIMS chip for applying an analyte on the subject's skin to the NIMS chip, wherein the mass spectrum comprises ions derived from the analyte; and identifying the mass spectrum pattern unique to the subject comprises detecting a pattern of the ions derived from the analyte.

2. The method of claim 1, wherein at least one of the ions is specific to the analyte.

3. A method of identifying an analyte on a subject's skin comprising:
generating a mass spectrum from a nanostructure-initiator mass spectrometry (NIMS) chip, wherein the chip comprises an analyte from the subject's skin;
identifying the analyte from the mass spectrum;
wherein generating the mass spectrum comprises contacting the subject's skin to the NIMS chip for applying an analyte on the subject's skin to the NIMS chip, wherein the mass spectrum comprises an ion derived from the analyte; and identifying the analyte from the mass spectrum comprises detecting the ion.

4. The method of claim 3, wherein the analyte comprises isotopes and the method further comprises identifying the origin of the analyte by determining a ratio of the isotopes indicative of the origin.

5. The method of claim 3, wherein the ion is specific to the analyte.

6. The method of claim 5, wherein the analyte is a chemical, microbe, metabolite produced by the subject, endogenous biomarker, animal substance, ingested substance, or environmental substance.

7. The method of claim 6, wherein the analyte is a microbe.

8. The method of claim 7, further comprising determining the origin of the subject's exposure to the microbe based on the identification of the microbe.

9. The method of claim 7, further comprising identifying a community of microbes on the skin.

10. The method of claim 9, further comprising determining the identity of the subject based on the identification of the community of microbes.

11. The method of claim 6, wherein the chemical is gunpowder, an explosive, a weapon, or a drug.

12. The method of claim 6, further comprising determining where the subject has been based on the identification of the analyte, wherein the identified analyte is indicative of a geographical location.

13. The method of claim 3, further comprising determining what the subject has been exposed to based on the identification of the analyte.

14. The method of claim 3, further comprising generating an image of a print of the subject's skin on the NIMS chip.

15. The method of claim 14, further comprising generating a fingerprint image of the subject.

16. The method of claim 3, wherein identifying the analyte by detecting the ion specific to the analyte comprises matching the detected ion with a known ion standard, pattern, or profile.

17. The method of claim 3, further comprising identifying a plurality of analytes on the subject's skin by detecting ions specific to the analytes, and determining a biometric pattern or profile from the identified analytes.

18. A method of generating a fingerprint comprising:
contacting a finger of a subject to a nanostructure-initiator mass spectrometry (NIMS) chip, thereby applying metabolites on the finger to the NIMS chip;
generating a mass spectrum at a plurality of sites on the NIMS chip contacted with the finger, wherein the mass spectrum comprises ions from the metabolites applied to the NIMS chip; and
reconstructing an image of the subject's finger from the mass spectrum generated at sites on the NIMS chip contacted with the finger, thereby generating a fingerprint.

19. The method of claim 18, wherein a mass spectrum is generated at every position of the NIMS chip in two dimensions at an x-y step-size of about 75 μm.

20. The method of claim 19, wherein reconstructing an image of the subject's finger comprises computationally reading each generated mass spectrum and storing the intensity information of each mass spectrum in a 2D array, wherein the first dimension represents the pixels and the second dimension represents the mass-to-charge (m/z) values of each mass spectrum.

21. A method of determining a physiological change in a subject comprising:
generating a fingerprint of the subject according to the method of claim 20 at a first and one or more later times; and
determining the difference in the fingerprints, which reflects a difference in mass spectrum ions at the first and later time, wherein the difference in the fingerprints indicates a physiological change in the subject.

22. The method of claim 21, wherein the physiological change is a change in health status of the subject.

23. The method of claim 22, wherein the change in health status reflects before and after taking medication or a healthcare product.

24. The method of claim 23, wherein the medication is an antibiotic or antibacterial agent.

25. A system for identifying a subject, comprising:
a nanostructure-initiator mass spectrometry (NIMS) chip;
an analysis module configured to read a fingerprint applied to the NIMS chip and determine a mass spectrum fingerprint pattern; and
a comparison module configured to compare the determined mass spectrum to a database of known patterns in order to identify the subject.

26. The system of claim 25, further comprising an analyte detection module configured to read the mass spectrum fingerprint and identify analytes associated with the fingerprint.

27. The system of claim 26, wherein the analyte detection module is configured to identify whether the analyte is a chemical, microbe, metabolite produced by the subject, endogenous biomarker, animal substance, ingested substance, or environmental substance.

28. The system of claim 25, wherein the analysis module is configured to determine a mass spectrum fingerprint by detecting ions derived from an analyte on the fingerprint.

29. The system of claim 28, wherein the comparison module is configured to identify the mass spectrum pattern unique to the subject by detecting a pattern of the ions derived from the analyte.

* * * * *